United States Patent
Bettouyashiki et al.

(10) Patent No.: US 10,959,691 B2
(45) Date of Patent: Mar. 30, 2021

(54) ELECTRONIC CASSETTE

(71) Applicant: FUJIFILM Corporation, Tokyo (JP)

(72) Inventors: Akihito Bettouyashiki, Ashigarakami-gun (JP); Makoto Kitada, Ashigarakami-gun (JP); Jun Enomoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/890,234

(22) Filed: Jun. 2, 2020

(65) Prior Publication Data

US 2020/0289072 A1    Sep. 17, 2020

Related U.S. Application Data

(60) Continuation of application No. 15/928,497, filed on Mar. 22, 2018, now Pat. No. 10,702,228, which is a
(Continued)

(30) Foreign Application Priority Data

Sep. 22, 2014 (JP) .................................. 2014-193132

(51) Int. Cl.
*A61B 6/00* (2006.01)
*H01Q 1/22* (2006.01)

(52) U.S. Cl.
CPC .......... *A61B 6/4283* (2013.01); *A61B 6/4291* (2013.01); *A61B 6/4411* (2013.01);
(Continued)

(58) Field of Classification Search
CPC ... A61B 6/4283; A61B 6/4291; A61B 6/4411; A61B 6/56; A61B 6/563; H01Q 1/22
See application file for complete search history.

(56) References Cited

U.S. PATENT DOCUMENTS 4,457,010 A * 6/1984 Jenkins ................ G03B 42/025
378/167
5,594,774 A * 1/1997 Schmidt ................ A61F 17/00
378/167
(Continued)

FOREIGN PATENT DOCUMENTS

JP    2002-186614 A    7/2002
JP    2003/210444 A    7/2003
(Continued)

OTHER PUBLICATIONS

Japanese Office Action, dated Aug. 1, 2018, for corresponding Japanese Application No. 2017-235883, along with an English translation.
(Continued)

*Primary Examiner* — Dani Fox
*Assistant Examiner* — Soorena Kefayati
(74) *Attorney, Agent, or Firm* — Birch, Stewart, Kolasch & Birch, LLP

(57) ABSTRACT

A housing of an electronic cassette has an inclined surface which is formed between a side surface and a rear surface thereof and inclined relative to the side surface and the rear surface. An antenna opening through which a radio wave is transmitted is formed on the inclined surface. Since the antenna opening is formed on the inclined surface, the antenna opening is not blocked by a rear plate of a holder of an upright radiographic stand or a supine radiographic stand, and the antenna opening is not blocked by a side panel of an outer grid. Both in the case where the electronic cassette is set to the holder and in the case where the outer grid is attached to the electronic cassette, it is possible to perform stable wireless communication.

16 Claims, 10 Drawing Sheets

Related U.S. Application Data division of application No. 14/838,743, filed on Aug. 28, 2015, now Pat. No. 9,955,931.

(52) U.S. Cl.
CPC ............... *A61B 6/56* (2013.01); *A61B 6/563* (2013.01); *H01Q 1/22* (2013.01)

(56) References Cited

U.S. PATENT DOCUMENTS

| | | | | |
|---|---|---|---|---|
| 6,919,569 | B2* | 7/2005 | Homme | H01L 27/14618 118/728 |
| 7,873,145 | B2* | 1/2011 | Liu | G03B 42/02 378/98.8 |
| 8,172,461 | B2 | 5/2012 | Liu et al. | |
| 8,256,957 | B1* | 9/2012 | Barnes | G01T 7/00 378/189 |
| 2009/0028299 | A1* | 1/2009 | Yoshimi | A61B 6/4494 378/189 |
| 2010/0148081 | A1* | 6/2010 | Yoshimi | A61B 6/4233 250/370.08 |
| 2011/0051902 | A1* | 3/2011 | Liu | A61B 6/4283 378/189 |
| 2011/0248173 | A1* | 10/2011 | Ogura | A61B 6/4283 250/361 R |
| 2012/0168632 | A1* | 7/2012 | Yagi | A61B 6/4233 250/366 |
| 2012/0228499 | A1* | 9/2012 | Koyanagi | G03B 42/04 250/336.1 |
| 2012/0314354 | A1* | 12/2012 | Rayner | H04M 1/18 361/679.01 |
| 2013/0068961 | A1* | 3/2013 | Tajima | G01T 1/17 250/394 |
| 2013/0077760 | A1* | 3/2013 | Tagawa | A61B 6/4291 378/154 |
| 2013/0083898 | A1* | 4/2013 | Tajima | G01D 18/00 378/97 |
| 2013/0259208 | A1* | 10/2013 | Watanabe | A61B 6/4411 378/182 |
| 2014/0125529 | A1* | 5/2014 | Park | H01Q 1/243 343/702 |
| 2014/0252229 | A1* | 9/2014 | Kondo | A61B 6/4283 250/336.1 |
| 2015/0164461 | A1* | 6/2015 | Imamura | H05G 1/44 378/97 |
| 2015/0320373 | A1* | 11/2015 | Rieuvernet | A61B 6/4405 378/189 |
| 2015/0351715 | A1* | 12/2015 | Ota | A61B 6/107 378/64 |
| 2015/0366524 | A1* | 12/2015 | Suzuki | A61B 6/4283 378/189 |
| 2016/0029984 | A1* | 2/2016 | Jang | A61B 6/547 378/189 |
| 2018/0212308 | A1* | 7/2018 | Vandenbosch | A61B 6/4283 |

FOREIGN PATENT DOCUMENTS

| | | |
|---|---|---|
| JP | 3137548 U | 11/2007 |
| JP | 3144690 U | 9/2008 |
| JP | 2009-053662 A | 3/2009 |
| JP | 2009-103609 A | 5/2009 |
| JP | 2011-050736 A | 3/2011 |
| JP | 2011-112923 A | 6/2011 |
| JP | 2013-72708 A | 4/2013 |
| JP | 2013-81768 A | 5/2013 |
| JP | 2013-205386 A | 10/2013 |
| JP | 2014-57831 A | 4/2014 |

OTHER PUBLICATIONS

Japanese Office Action, dated Jan. 22, 2019, for corresponding Japanese Application No. 2017-235883, with an English translation.
Notice of Allowance in corresponding U.S. Appl. No. 14/838,743 dated Dec. 22, 2017.
Notice of Allowance dated Mar. 3, 2020 in corresponding U.S. Appl. No. 15/928,497.
Notification of Reasons for Refusal issued in corresponding Japanese Patent Application No. 2014-193132 dated May 31, 2017, with English language translation (6 pages).
Office Action in corresponding U.S. Appl. No. 14/838,743 dated Mar. 9, 2017.
Office Action in corresponding U.S. Appl. No. 14/838,743 dated Oct. 19, 2017.
Office Action dated Apr. 29, 2019 in corresponding U.S. Appl. No. 15/928,497.
Office Action dated Nov. 1, 2019 in corresponding U.S. Appl. No. 15/928,497.

\* cited by examiner

ELECTRONIC CASSETTE

CROSS-REFERENCE TO RELATED APPLICATIONS

This application is a Continuation of copending application Ser. No. 15/928,497 filed Mar. 22, 2018, which is a Divisional of application Ser. No. 14/838,743 filed on Aug. 28, 2015, issued as U.S. Pat. No. 9,955,931 on May 1, 2018, which claims priority under 35 U.S.C. § 119 to Japanese Patent Application No. 2014-193132, filed Sep. 22, 2014. Each of the above applications is hereby expressly incorporated by reference, in its entirety, into the present application.

BACKGROUND OF THE INVENTION

1. Field of the Invention

The present invention relates to an electronic cassette for use in radiography.

2. Description Related to the Prior Art

An electronic cassette has been widely used in medical radiography, for example, in X-ray photography. The electronic cassette is a portable X-ray image detector provided with an built-in image detector (also referred to as a flat panel detector (FPD)) for detecting an X-ray image of a subject such as a patient inside a housing having a front surface on which X-rays are incident, a rear surface facing the front surface, and four side surfaces.

As shown in FIG. 1 in Japanese Patent Laid-Open Publication No. 2014-057831, an electronic cassette is set to be attachable to and detachable from a holder of an upright radiographic stand or a supine radiographic stand, such that the electronic cassette is held in a posture in which an X-ray source for irradiating X-rays and a front surface of a housing face each other. The holder has a front plate for covering the front surface of the housing and a rear plate for covering a rear surface of the housing. The holder is made of an electrically-conductive material having electromagnetic wave shielding properties.

Further, in X-ray photography, since scattered rays are generated upon transmission of X-rays through a subject, a grid for removing the scattered rays is used in some cases. There is a grid detachably attached to an electronic cassette externally (hereinafter referred to as external grid) (see Utility Model Registration No. 3137548 and Utility Model Registration No. 3144690). The external grid is not attached to an electronic cassette in the case where the electronic cassette is set to a holder of an upright radiographic stand or a supine radiographic stand. The external grid is attached to an electronic cassette in the case where the electronic cassette is used alone for a subject lying on a bed or a subject who cannot move on his/her own such as an aged person or an emergency patient.

The external grid consists of a grid body and a holding frame for holding the grid body. The grid body is attached to the holding frame. The holding frame has a top panel for covering the front surface of the housing, and a side panel which is provided to an edge of the top panel and extends in a direction from a front-surface side of the housing to a rear-surface side thereof so as to cover part of a side surface of the housing. The holding frame is made of an electrically-conductive material having electromagnetic wave shielding properties in the same manner as the holder of the radiographic stand.

There is an electronic cassette, which is provided with a wireless communication section for wireless communication with an external device such as a control device for controlling operation of the electronic cassette and a battery for supplying electricity to activate the electronic cassette, such that the electronic cassette can be used without a cable. For example, United States Patent Application Publication No. 2012/0228499 corresponding to Japanese Patent Laid-Open Publication No. 2011-112923 discloses an electronic cassette incorporating an antenna of a wireless communication section provided at a surface facing an X-ray incident surface of an image detector in a housing.

The housing is made of an electrically-conductive material having electromagnetic wave shielding properties in the same manner as a holder of an radiographic stand and a holding frame of an external grid in order to prevent electromagnetic noise from entering the electronic cassette and prevent electromagnetic noise from being emitted from the electronic cassette to the outside. According to United States Patent Application Publication No. 2012/0228499, the antenna is incorporated in the housing as descried above, and an antenna opening through which a radio wave is transmitted is formed on a rear surface or a side surface of the housing, such that transmission/reception of the radio wave through the antenna can be performed. According to Japanese Patent Laid-Open Publication No. 2014-057831, a cover having radio wave transmission properties is attached to an antenna opening.

However, there are the following problems in the case where the antenna opening is formed on the rear surface or the side surface of the housing as disclosed in Japanese Patent Laid-Open Publication No. 2014-057831.

In the case where the antenna opening is formed on the rear surface of the housing, when the electronic cassette is set to the holder of the radiographic stand, the rear plate of the holder having electromagnetic wave shielding properties blocks the antenna opening formed on the rear surface of the housing in some cases. In the case where the antenna opening is formed on the side surface of the housing, when the outer grid is attached to the housing, the side panel of the holding frame having electromagnetic wave shielding properties blocks the antenna opening formed on the side surface of the housing in some cases.

In the case where the antenna opening is blocked by a member having electromagnetic wave shielding properties such as the holder of the radiographic stand and the outer grid, the radio wave transmission properties are decreased or wireless communication speed is reduced, or even worse, the wireless communication is sometimes disconnected. Therefore, it becomes impossible to perform stable wireless communication.

Incidentally, in the case where the antenna opening is formed on not the rear surface or the side surface of the housing but a front surface of the housing, since the front surface of the housing is blocked by the front plate of the holder of the radiographic stand or the top panel of the outer grid in the similar manner as the rear surface and the side surface of the housing. Therefore, it is not appropriate to form the antenna opening on the front surface as well as the rear surface and the side surface.

In the case where the antenna opening is formed on any of the side surface, the rear surface, and the front surface of the housing as described above, in a usage environment in which the electronic cassette is set to the holder of the radiographic stand or in which the outer grid is attached to the electronic cassette, it is impossible to perform stable wireless communication in some cases.

Thus, in the case where the antenna opening is blocked by the member having electromagnetic wave shielding properties such as the holder of the radiographic stand and the outer grid, it may be possible to improve the radio wave transmission properties at any rate by processing a portion of the member blocking the antenna opening, for example, by cutting out the portion of the member blocking the antenna opening or making a hole on the portion of the member blocking the antenna opening, such that the shape of the portion of the member blocking the antenna opening corresponds to the shape of the antenna opening. However, such processing is troublesome. Additionally, the strength of the member may be deteriorated in some cases.

SUMMARY OF THE INVENTION

In view of the foregoing, an object of the present invention is to provide an electronic cassette capable of performing stable wireless communication without requiring troublesome processing regardless of a usage environment.

To achieve the above object of the present invention, an electronic cassette of the present invention includes an image detector for detecting a radiation image of a subject based on radiation having been transmitted through the subject, a housing for housing the image detector, an antenna disposed inside the housing for use in wireless transmission of at least the radiation image via radio waves, and an antenna opening through which the radio waves are transmitted. The housing has a front surface on which the radiation is incident, a rear surface facing the front surface, and four side surfaces. Additionally, the housing has an inclined surface which is formed at least between one of the side surfaces and the rear surface and inclined relative to the one of the side surfaces and the rear surface. At least part of the antenna opening is formed on the inclined surface.

The antenna is preferably installed at a position facing the antenna opening.

Preferably, the electronic cassette further includes a cover for blocking the antenna opening.

Preferably, a width of the inclined surface corresponding to a distance between a first boundary that is a boundary between the side surface and the inclined surface of the housing and a second boundary that is a boundary between the rear surface and the inclined surface of the housing is larger than a width of the side surface in a thickness direction of the housing that is perpendicular to the front surface and the rear surface.

Preferably, the electronic cassette is set to be attachable to and detachable from a holder of a radiographic stand. The holder preferably includes a front plate for covering the front surface of the housing, and a rear plate for covering the rear surface of the housing. The rear plate faces the front plate.

Preferably, an outer grid is detachably attached to the housing in order to remove scattered rays generated upon transmission of the radiation through the subject. Preferably, the outer grid includes a top panel for covering the front surface of the housing, and a side panel which is provided to an edge of the top panel and extends in a direction from a front-surface side of the housing to a rear-surface side thereof so as to cover part of the side surface of the housing.

According to the present invention, since the antenna opening is formed on the inclined surface which is inclined relative to the side surface and the rear surface of the housing, the antenna opening is not blocked by the holder of the radiographic stand and the outer grid. Therefore, it is possible to provide the electronic cassette capable of performing stable wireless communication without requiring troublesome processing regardless of a usage environment.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
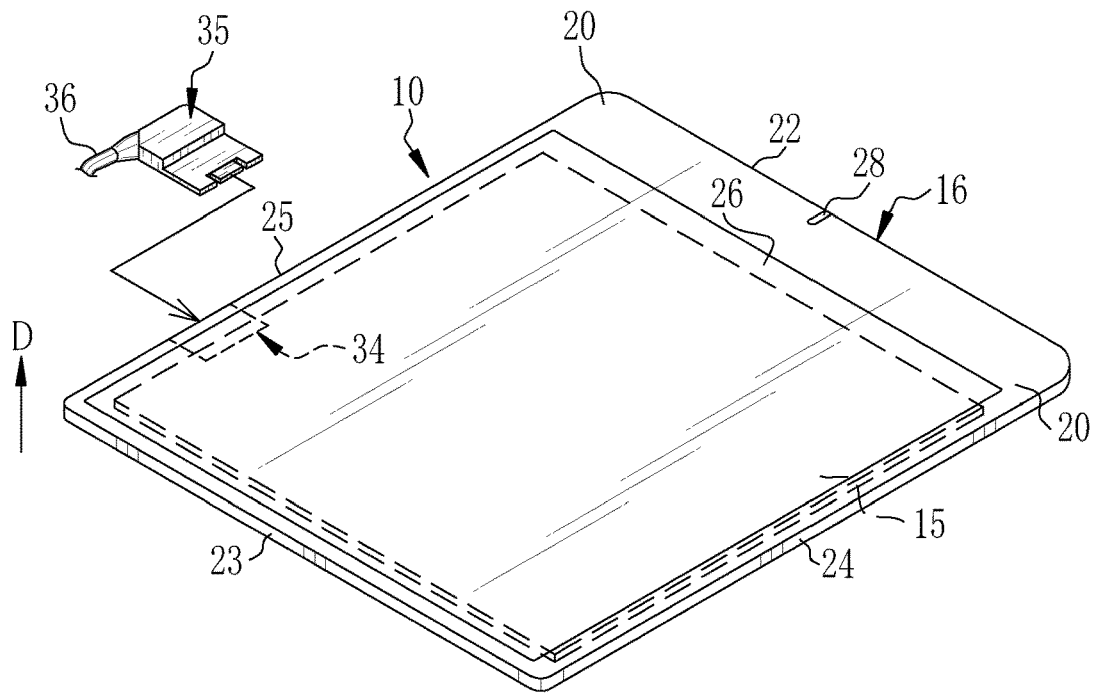
FIG. 1 is a perspective view illustrating an external appearance of an electronic cassette as viewed from a front side thereof.
Figure 2:
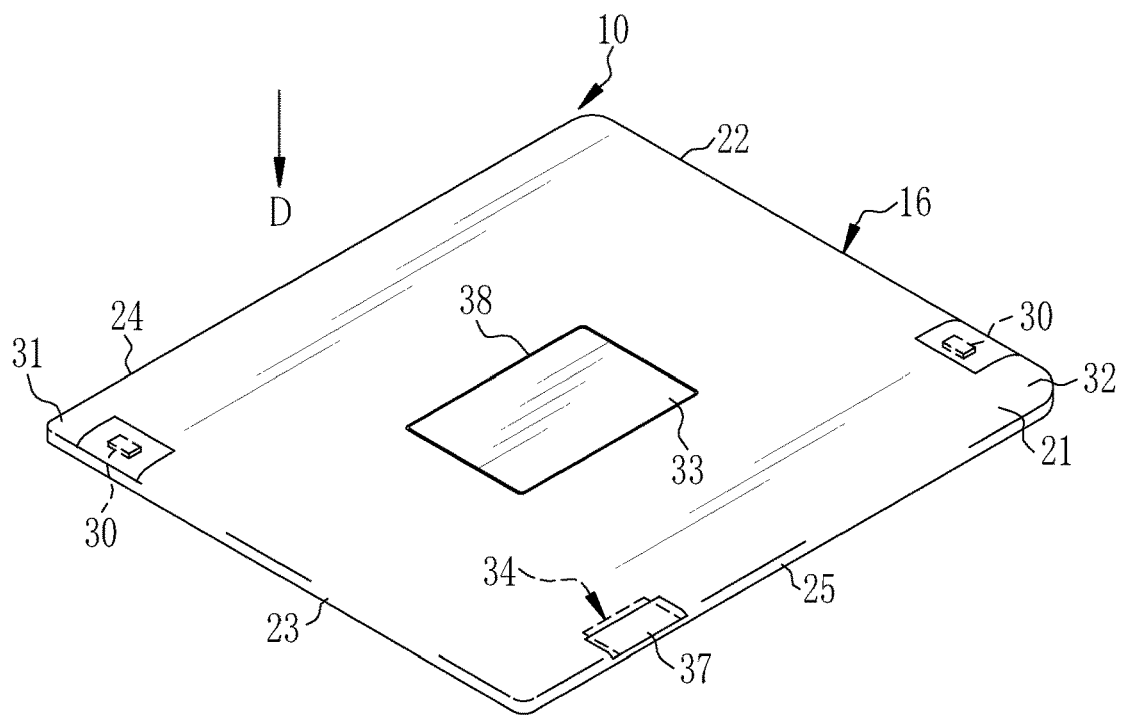
FIG. 2 is a perspective view illustrating an external appearance of the electronic cassette as viewed from a rear side thereof.

In FIGS. 1 and 2, an electronic cassette 10 is used for medical X-ray photography, for example, and consists of an image detector 15 and a portable housing 16 for housing the image detector 15. The image detector 15 detects an X-ray image of a subject H (see FIG. 3) based on X-rays having been transmitted through the subject H.

As well known, the image detector 15 includes a scintillator (phosphor) for converting incident X-rays into visible light beams, and a thin film transistor (TFT) active matrix substrate having a plurality of pixels each of which accumulates charge corresponding to the visible light beams from the scintillator. The housing 16 incorporates not only the image detector 15 but also a gate driver, a signal processing circuit, a control section, and the like. The gate driver supplies a gate pulse to a gate of the TFT to switch the TFT. The signal processing circuit converts the charge accumulated in each of the pixels into a voltage signal representing an X-ray image and outputs the voltage signal. The control section controls operation of each of the gate driver and the signal processing circuit.

The housing 16 consists of a front surface 20 on which the X-rays are incident, a rear surface 21 facing the front surface 20, and four side surfaces 22, 23, 24, and 25, so as to have a rectangular parallelepiped shape. The housing 16 is made of metal which shields an electromagnetic wave (such as aluminum, magnesium, and alloy of them) or an electrically-conductive material such as carbon, for example. The housing 16 also functions as an electromagnetic shield for preventing electromagnetic noise from entering the electronic cassette 10 and preventing electromagnetic noise from being emitted from the electronic cassette 10 to the outside. The housing 16 has a size compliant with the ISO (International Organization for Standardization) 4090: 2001 which is substantially the same as the size of each of a film cassette, an IP (Imaging Plate) cassette, and a CR (Computed Radiography) cassette, for example.

A rectangular opening is formed on the front surface 20 of the housing 16. A transmission plate 26 is attached to the opening. A protection film 27 (see FIG. 6) made of a resin, through which the X-rays are transmitted, is adhered to a surface of the transmission plate 26. This allows the front surface 20 to be a flat surface. The transmission plate 26 is made of a carbon material which is lightweight, highly rigid, and extremely permeable to the X-rays. Additionally, an indicator 28 such as an LED (Light Emitting Diode) is disposed on the front surface 20 at the side of the side surface 22 so as to indicate power on/off of the electronic cassette 10.

The housing 16 incorporates a control device (not shown) for controlling the operation of the electronic cassette and a wireless communication section 30 for wireless communication of various kinds of information such as X-ray images. The wireless communication section 30 is disposed one-by-one at two corners including a corner 31 as an intersection of the side surface 23 and the side surface 24, and a corner 32 as an intersection of the side surface 22 and the side surface 25. The corner 31 and the corner 32 face each other. Therefore, even if the wireless communication using one of the two wireless communication sections 30 is in a poor condition, wireless communication can be performed in a state that the other of the two wireless communication sections 30 is in a stable condition.

In the case where the wireless communication section 30 is used, the electronic cassette 10 is activated by the electricity from a battery 33, namely, the electronic cassette 10 can be used without a cable. Although the two wireless communication sections 30 are disposed at different positions, the two wireless communication sections 30 have the same structure, and function in the same manner. Therefore, only the wireless communication section 30 disposed at the corner 31 is explained hereinbelow.

Further, the electronic cassette 10 includes a female connector 34 which functions for wired communication with the control device. A male connector 35 is connected to the female connector 34. One end of a cable 36 for wired connection between the electronic cassette 10 and the control device is connected to the male connector 35. The other end of the cable 36 is connected to a connector (not shown) connected to the control device. During the use of the wireless communication function, the female connector 34, to which the male connector 35 is not connected, is covered and protected by a lid 37.

The electronic cassette 10 receives not only the various kinds of information but also electricity through the female connector 34 from the control device. In the case where the female connector 34 and the male connector 35 are connected to each other, the electronic cassette 10 is activated by the electricity from the control device. It is also possible to charge the battery 33 with use of the electricity from the control device.

A battery mounting section 38 is formed at the center of the rear surface 21. The battery 33 for supplying electricity to activate the electronic cassette 10 is detachably mounted on the battery mounting section 38. FIG. 2 shows a state that the battery 33 is mounted on the battery mounting section 38.

The battery mounting section 38 is a concave portion in which the rear surface 21 is recessed toward the front surface 20. The battery mounting section 38 is formed to have the same planar shape and the same planar size as those of the battery 33, such that the battery 33 is fit into the battery mounting section 38 substantially without a gap. Additionally, the depth of the battery mounting section 38 from the rear surface 21 is substantially the same as the thickness of the battery 33. Therefore, in a state that the battery 33 is mounted on the battery mounting section 38 as shown in FIG. 2, an upper surface of the battery 33 is exposed through the rear surface 21, and the upper surface of the battery 33 and the rear surface 21 are on the same plane.

Figure 3:
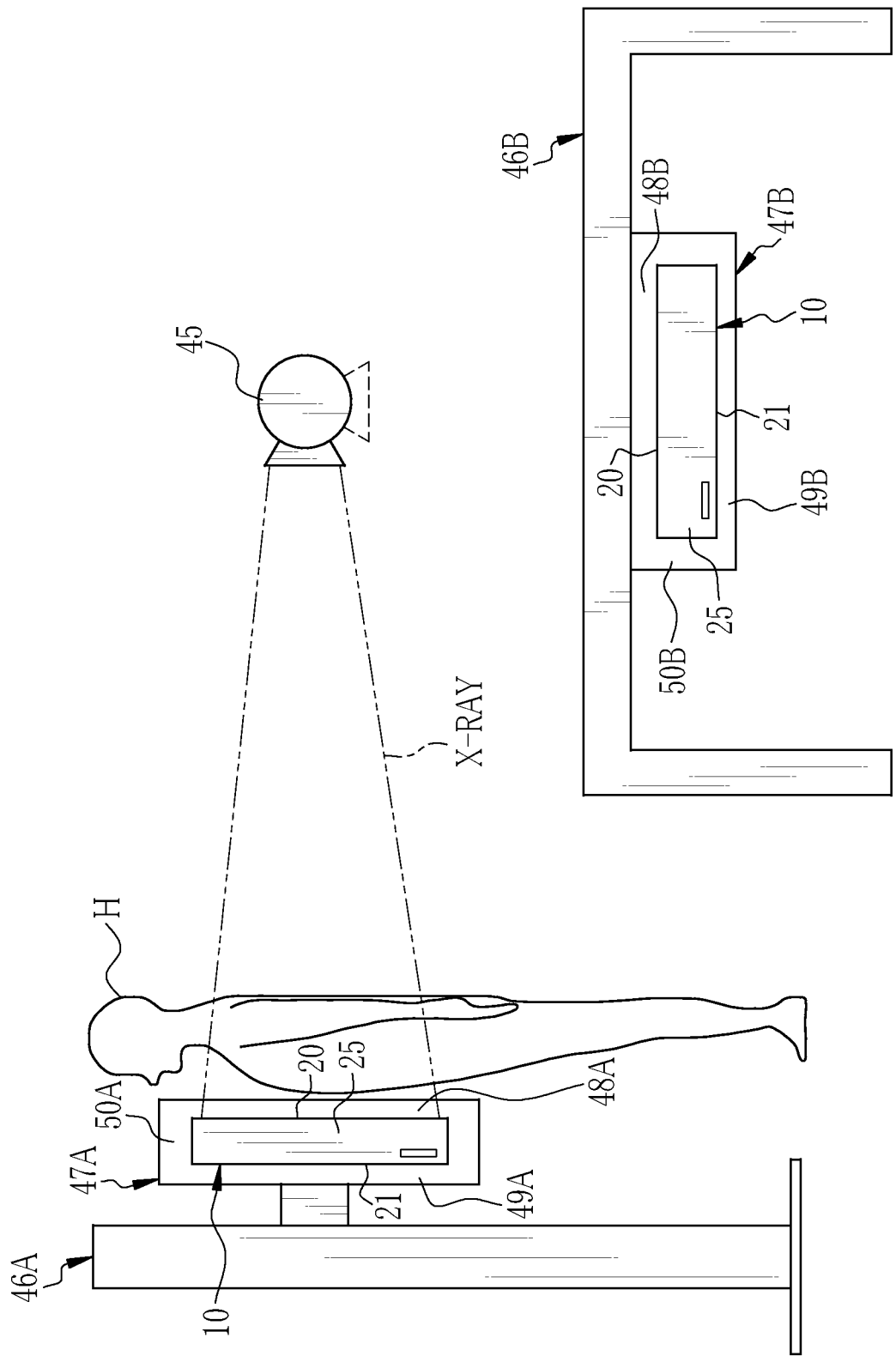
FIG. 3 is a plan view illustrating an external appearance of each of an upright radiographic stand and a supine radiographic stand.

As shown in FIG. 3, the electronic cassette 10 is set to be attachable to and detachable from a holder 47A of an upright radiographic stand 46A or a holder 47B of a supine radiographic stand 46B, such that the electronic cassette 10 is held in a posture in which an X-ray source 45 for irradiating X-rays and the front surface 20 of the housing 16 face each other. FIG. 3 shows a state that the electronic cassette 10 is set to the holder 47A of the upright radiographic stand 46A to perform X-ray photography.

Each of the holders 47A and 47B is made of an electrically-conductive material having electromagnetic wave shielding properties such as aluminum and stainless. The holder 47A includes a front plate 48A for covering the front surface 20 of the housing 16, a rear plate 49A for covering the rear surface 21 of the housing 16, and a side plate 50A for covering the side surfaces 22 to 24 out of the side surfaces 22 to 25 of the housing 16. The reason why the surface 25 is excluded is that the side surface 25 is provided with the female connector 34. The rear plate 49A faces the front plate 48A. Similarly, the holder 47B includes a front plate 48B for covering the front surface 20 of the housing 16, a rear plate 49B for covering the rear surface 21 of the housing 16, and a side plate 50B for covering the side surfaces 22 to 24 out of the side surfaces 22 to 25 of the housing 16. The rear plate 49B faces the front plate 48B. Since the side surface 25 provided with the female connector 34 is exposed outside, the female connector 34 and the male connector 35 can be connected to each other in a state that the electronic cassette 10 is set to the holder 47A or the holder 47B.

Further, the electronic cassette 10 is used alone for the subject H lying on a bed or the subject H who cannot move on his/her own such as an aged person or an emergency patient, in addition to being set to the holder 47A of the upright radiographic stand 46A or the holder 47B of the supine radiographic stand 46B, in some cases. Furthermore, in the case where the housing 16 has substantially the same size as that of each of the film cassette, the IP cassette, and the CR cassette, the electronic cassette 10 can be attached to an existing radiographic stand for these cassettes.

Figure 4:
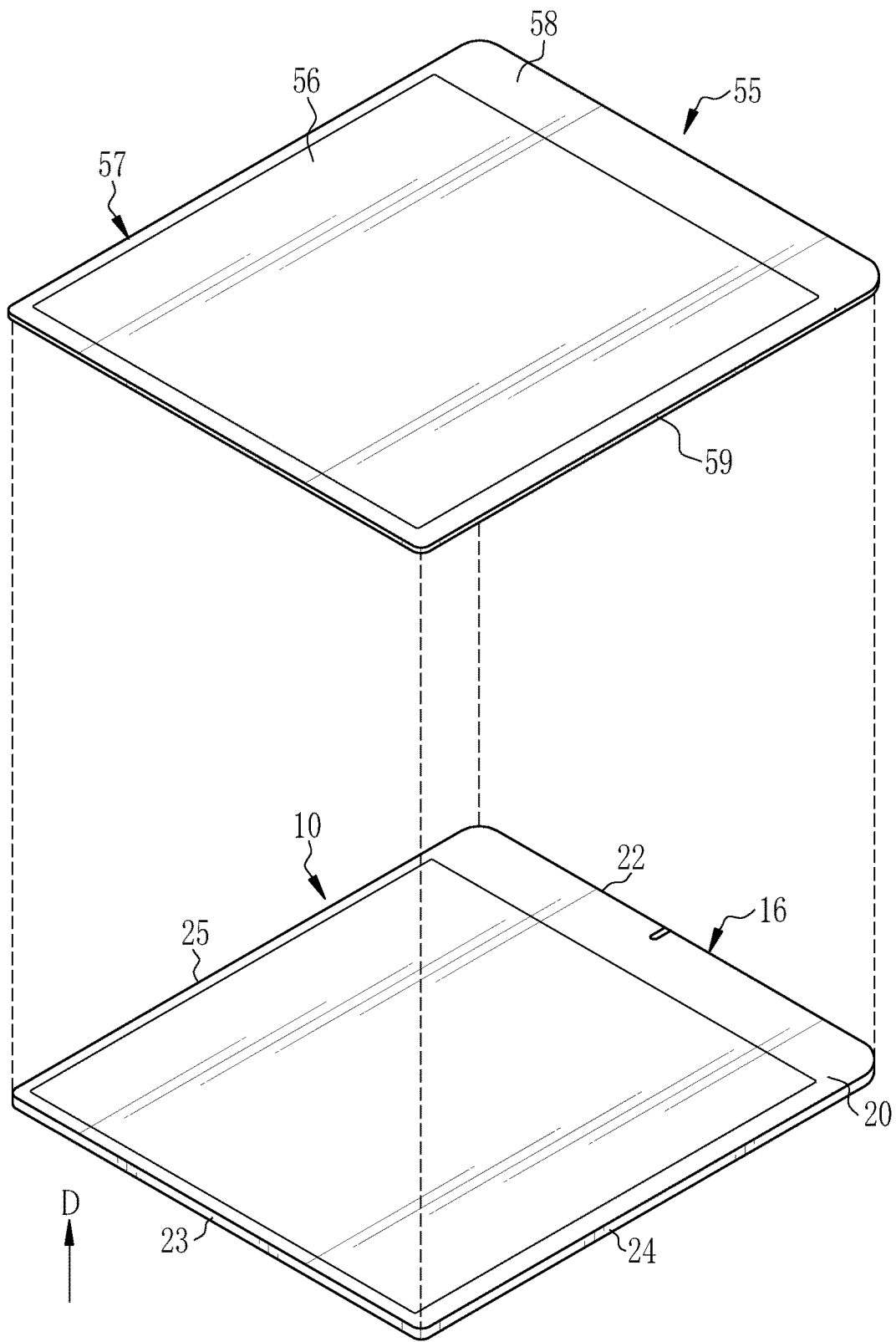
FIG. 4 is a perspective view illustrating an external appearance of each of an outer grid and the electronic cassette.

In X-ray photography, since scattered rays are generated upon transmission of X-rays through the subject H, an outer grid 55 shown in FIG. 4 is used for the purpose of removing the scattered rays in some cases in the case where the electronic cassette 10 is used alone. The outer grid 55 is detachably attached to the housing 16 externally. The outer grid 55 consists of a rectangular grid body 56 and a holding frame 57 for holding the grid body 56. The grid body 56 is slightly larger than the transmission plate 26 so as to cover the entire transmission plate 26 in the case where the outer grid 55 is attached to the housing 16. Further, the holding frame 57 is made of an electrically-conductive material having electromagnetic wave shielding properties such as aluminum and stainless. The holding frame 57 is slightly larger than the housing 16.

The holding frame 57 has a top panel 58 and a side panel 59. The top panel 58 has a rectangular opening to which the grid body 56 is attached. In the case where the outer grid 55 is attached to the housing 16, the top panel 58 and the grid body 56 cover the front surface 20 of the housing 16. The side panel 59 is provided to an edge of the top panel 58, and extends in a direction from the front surface 20 toward the rear surface 21. Incidentally, although not being shown in the drawing, the holding frame 57 is provided with a well-known dropping prevention/dropping prevention releasing mechanism. The dropping prevention/dropping prevention releasing mechanism fixes the outer grid 55 to the housing 16 so as to prevent the outer grid 55 from being dropped, and releases the dropping prevention.

Figure 5:
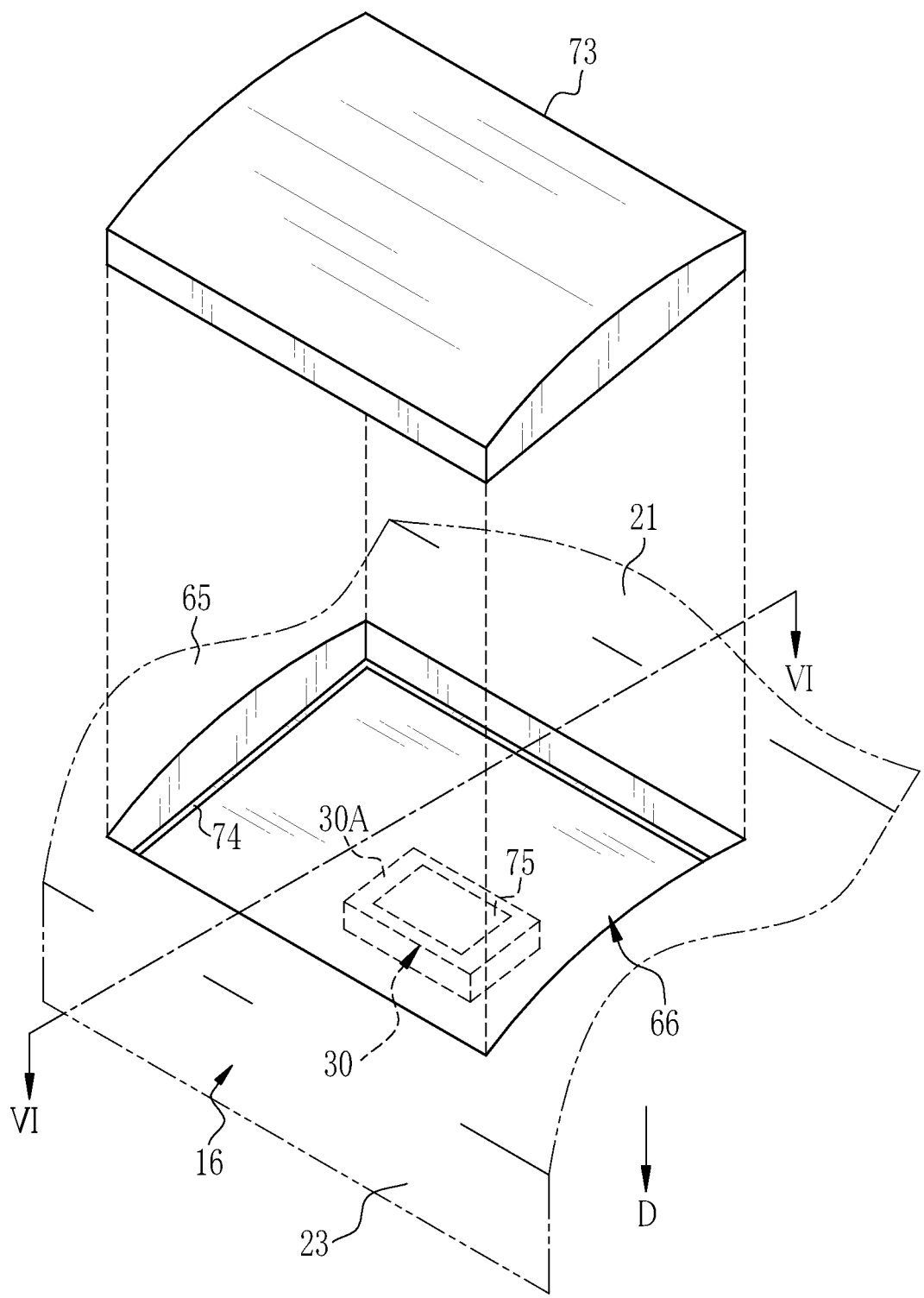
FIG. 5 is a perspective view illustrating an external appearance of a wireless communication section and its periphery.
Figure 6:
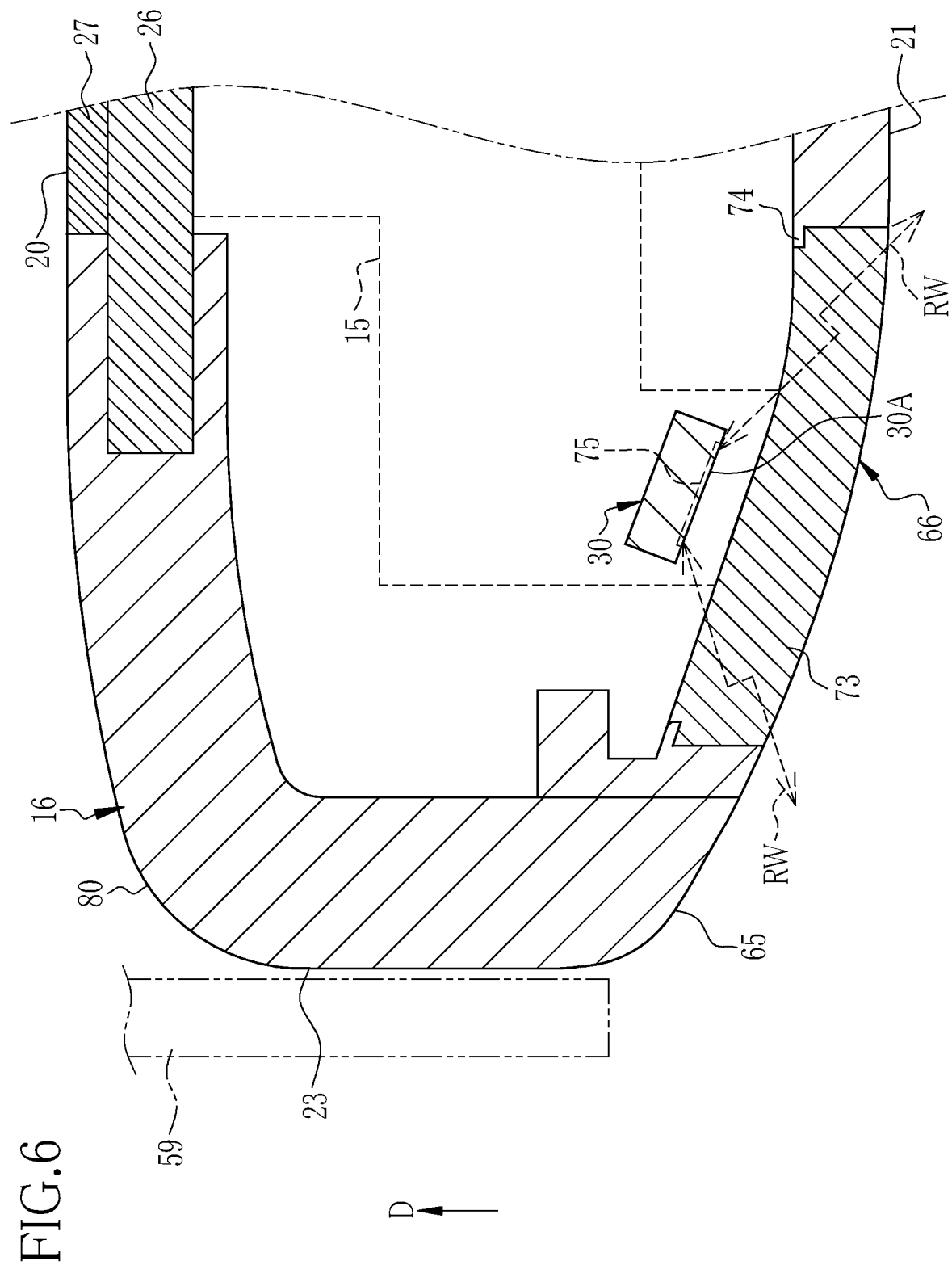
FIG. 6 is a cross-sectional view of the electronic cassette taken along a line VI-VI of FIG. 5.

FIG. 5 shows the wireless communication section 30 and its periphery. FIG. 6 is a cross-sectional view of the housing 16 taken along a line VI-VI of FIG. 5. In FIGS. 5 and 6, an inclined surface 65, which is inclined relative to the side surface 23 and the rear surface 21, is formed between the side surface 23 and the rear surface 21. An antenna opening 66 through which a radio wave is transmitted is formed on the inclined surface 65.

The antenna opening 66 has a rectangular shape as viewed from a direction D shown in FIGS. 5 and 6. An edge portion 74 is formed on an inner periphery of the antenna opening 66 so as to receive a cover 73. The edge portion 74 regulates an attachment position of the cover 73 in an insertion direction of the cover 73 into the antenna opening 66.

The wireless connection section 30 includes an antenna 75 and an oscillation circuit (not shown). The wireless connection section 30 is attached to a base on which the image detector 15 is mounted, for example, in the housing 16. The antenna 75 of the wireless connection section 30 emits a radio wave RW toward the control device and receives a radio wave RW from the control device. The radio wave RW from the antenna 75 is emitted through the antenna opening 66 to the outside of the housing 16. Further, the radio wave RW from the control device enters the inside of the housing 16 through the antenna opening 66.

The antenna 75 is installed at a position facing the antenna opening 66. More specifically, the antenna 75 is installed to be located substantially at the center of the antenna opening 66 such that an installation surface 30A of the wireless communication section 30, on which the antenna 75 is installed, is substantially parallel to the inclined surface 65.

The cover 73 is made of a non-conductive material having radio wave transmission properties such as resin. The cover 73 has the same shape and the same size as those of the antenna opening 66 such that the cover 73 is fit into the antenna opening 66 substantially without a gap. In a state that the cover 73 is fit into the antenna opening 66 as shown in FIG. 6, the upper surface of the cover 73 and the inclined surface 65 are on the same plane. The cover 73 and the antenna opening 66 are bonded to each other with use of an adhesive, for example. The antenna opening 66 is blocked by the cover 73 in a water-tight manner and in an air-tight manner.

The side panel 59 of the outer grid 55 has a length enough to reach a boundary between the side surface 23 and the inclined surface 65 (i.e., first boundary 85, see FIG. 7) shown by chain double-dashed lines in FIG. 6, for example, so as to facilitate the positioning of the outer grid 55 relative to the housing 16. Therefore, in the case where the outer grid 55 is attached to the housing 16, the side surface 23 is covered by the side panel 59.

The reference numeral 80 denotes an inclined surface formed between the side surface 23 and the front surface 20 in the similar manner as the inclined surface 65. Each of the inclines surfaces 65 and 80 is a curved surface which is convex toward the outside of the housing 16. Incidentally, although not shown in the drawing, the inclined surface 65 is also formed between the rear surface 21 and the side surfaces 22, 24, and 25, respectively, and the inclined surface 80 is also formed between the front surface 20 and the side surfaces 22, 24, and 25, respectively, in the similar manner as the side surface 23.

Figure 7:
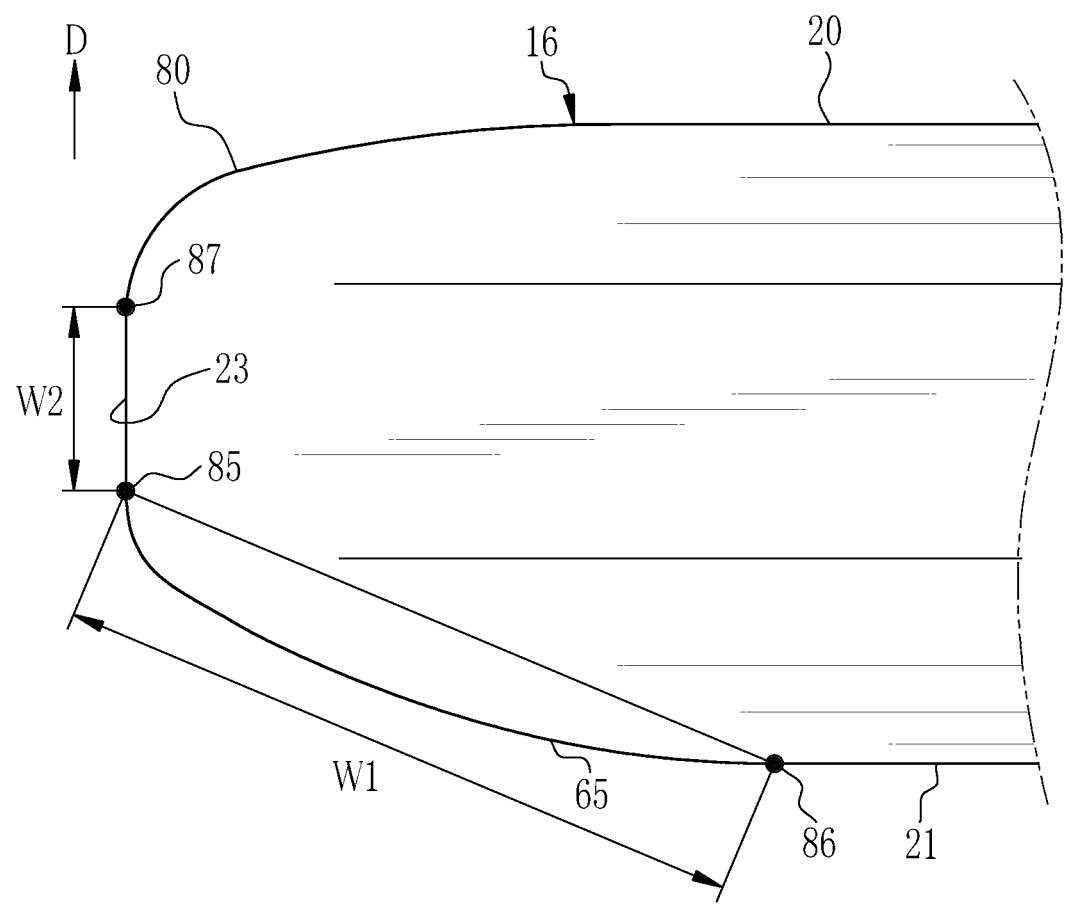
FIG. 7 is a view showing a width of each of an inclined surface and a side surface of a housing.

In FIG. 7, the inclined surface 65 has a width W1 larger than a width W2 of the side surface 23 in the direction D. The width W1 of the inclined surface 65 corresponds to a distance between the first boundary 85 that is a boundary between the side surface 23 and the inclined surface 65 and a second boundary 86 that is a boundary between the rear surface 21 and the inclined surface 65. Further, in other words, the width W2 of the side surface 22 corresponds to a distance between the first boundary 85 and a third boundary 87 that is a boundary between the side surface 22 and the inclined surface 80. Incidentally, in the similar manner as the side surface 23, the width W1 of the inclined surface 65 is larger than the width of each of the side surfaces 22, 24, and 25.

Figure 8:
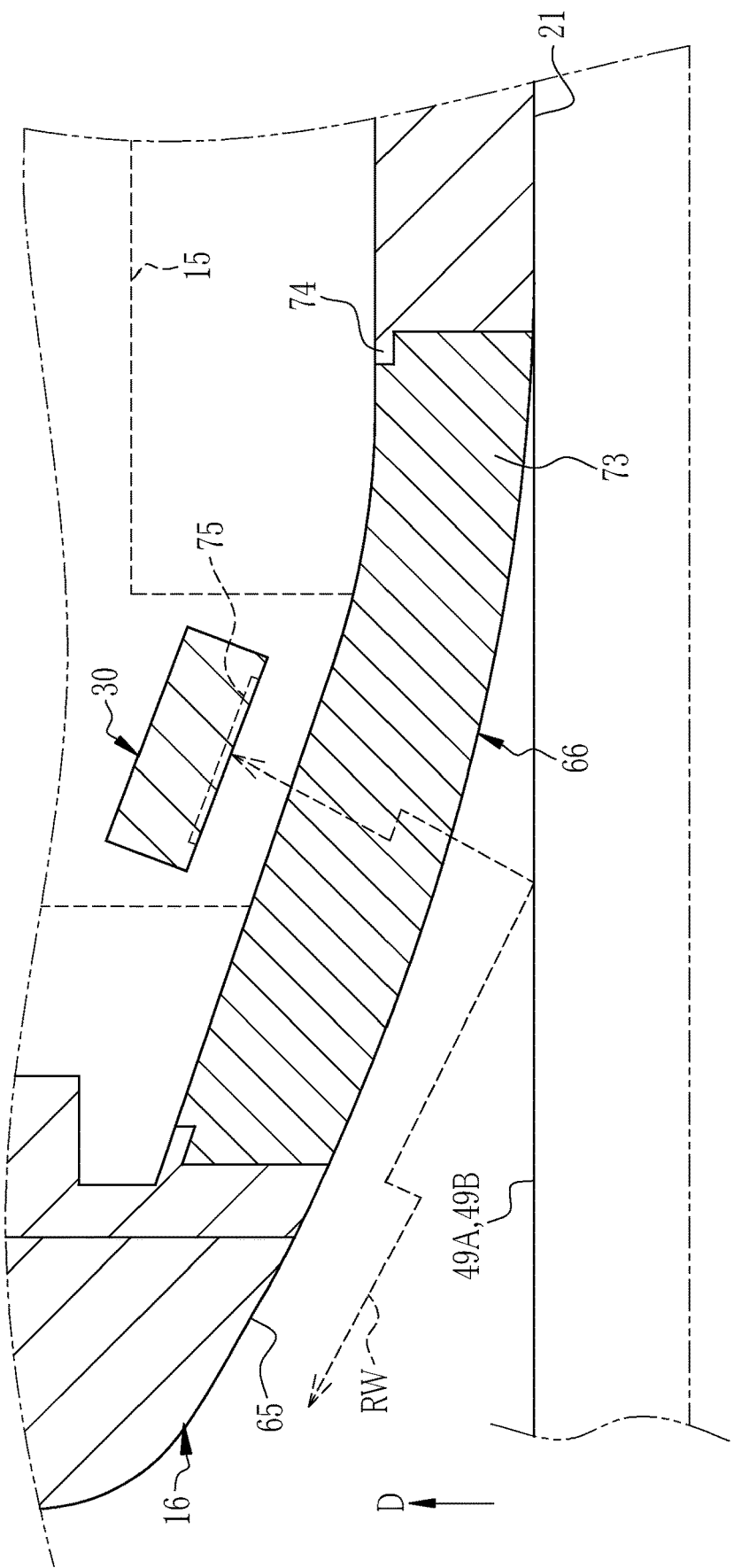
FIG. 8 is a view showing a propagation passage of a radio wave in the case where the electronic cassette is set to a holder of the upright radiographic stand or the supine radiographic stand.

Next, an operation of the above configuration is explained. As a preparation for X-ray photography, as shown in FIG. 3, the electronic cassette 10 is set to the holder 47A of the upright radiographic stand 46A or the holder 47B of the supine radiographic stand 46B, such that the electronic cassette 10 is held in a posture in which an X-ray source 45 and the front surface 20 face each other. In this case, the rear surface 21 is covered by the rear plate 49A of the holder 47A or the rear plate 49B of the holder 47B, as shown in FIG. 8. Therefore, in the case where the antenna opening 66 is formed on the rear surface 21, the antenna opening 66 is blocked by the rear plate 49A or 49B. When the antenna opening 66 is blocked by the rear plate 49A or 49B, emission of the radio wave RW through the antenna opening 66 or incidence of the radio wave RW through the antenna opening 66 is hindered. As a result, it becomes impossible to perform stable wireless communication.

However, according to this embodiment, the housing 16 has the inclined surface 65 inclined relative to the side surface 23 and the rear surface 21 thereof, and the antenna opening 66 is formed on the inclined surface 65. Therefore, the antenna opening 66 is not blocked by the rear plate 49A or 49B. In other words, there is secured a sufficient gap for emission or incidence of the radio wave RW between the inclined surface 65 and the rear plate 49A or 49B.

The radio wave RW is emitted from the antenna 75 to the outside of the housing 16 through the antenna opening 66, passes through the gap between the inclined surface 65 and the rear plate 49A or 49B, and then reaches the rear plate 49A or 49B. The radio wave RW, which has reached the rear plate 49A or 49B, reflects on the rear plate 49A or 49B and housing 16 several times, to be emitted to the outside of the holder 47A or 47B. The radio wave RW from the control device enters the housing 16 through the antenna opening 66 by following a path opposite to that of the radio wave RW emitted from the antenna 75, and is received by the antenna 75. Consequently, even in the case where the electronic cassette 10 is set to the holder 47A of the upright radiographic stand 46A or the holder 47B of the supine radiographic stand 46B, it is possible to perform stable wireless communication.

Additionally, in the case where the electronic cassette 10 is inserted into a clearance between the subject H lying on a bed and the bed to perform X-ray photography, there is secured a sufficient gap for emission or incidence of the radio wave RW between the inclined surface 65 and the bed, and therefore the same effect can be achieved.

In the case where the electronic cassette 10 is used alone in X-ray photography, the outer grid 55 is attached to the housing 16 in order to remove the scattered rays generated upon transmission of X-rays through the subject H.

A comparison example shown in FIG. 9, in which an antenna opening 90 is formed on the side surface 23, is considered hereinbelow. The antenna opening 90 is blocked by a cover 91. The antenna 75 is installed at a position facing the antenna opening 90.

In this case, for example, in the case where the outer grid 55 provided with the side panel 59 having a length enough to reach the first boundary 85 shown by chain double-dashed lines in FIG. 6 is attached to the housing 16, the antenna opening 90 is blocked by the side panel 59. Therefore, also in this case, the emission and incidence of the radio wave RW is hindered by the side panel 59, as with the case where the antenna opening 66 is blocked by the rear plate 49A or 49B. As a result, it becomes impossible to perform stable wireless communication.

However, according to this embodiment, the antenna opening 66 is formed on not the side surface 23 but the inclined surface 65, and therefore the antenna opening 66 is not blocked by the side panel 59, as shown in FIG. 6. Accordingly, even in the case where the outer grid 55 is attached to the electronic cassette 10, it is possible to perform stable wireless communication.

As described above, the processing such as cutting out a portion of the rear plate 49A or 49B and the side panel 59 blocking the antenna opening 66 or making a hole on the portion of the rear plate 49A or 49B and the side panel 59 blocking the antenna opening 66 is not necessary, and it is possible to perform stable wireless communication regardless of a usage environment in which the electronic cassette 10 is set to the holder 47A of the upright radiographic stand 46A or the holder 47B of the supine radiographic stand 46B or a usage environment in which the outer grid 55 is attached to the electronic cassette 10.

Consequently, it becomes unnecessary to provide a plurality of the wireless communication sections 30 in preparation for the case where the wireless communication using a certain wireless communication section is in a poor condition and another wireless communication section is used to perform the wireless communication. Thus, it is sufficient that the number of the wireless communication sections 30 is about two as in the case of the above embodiment.

Figure 9:
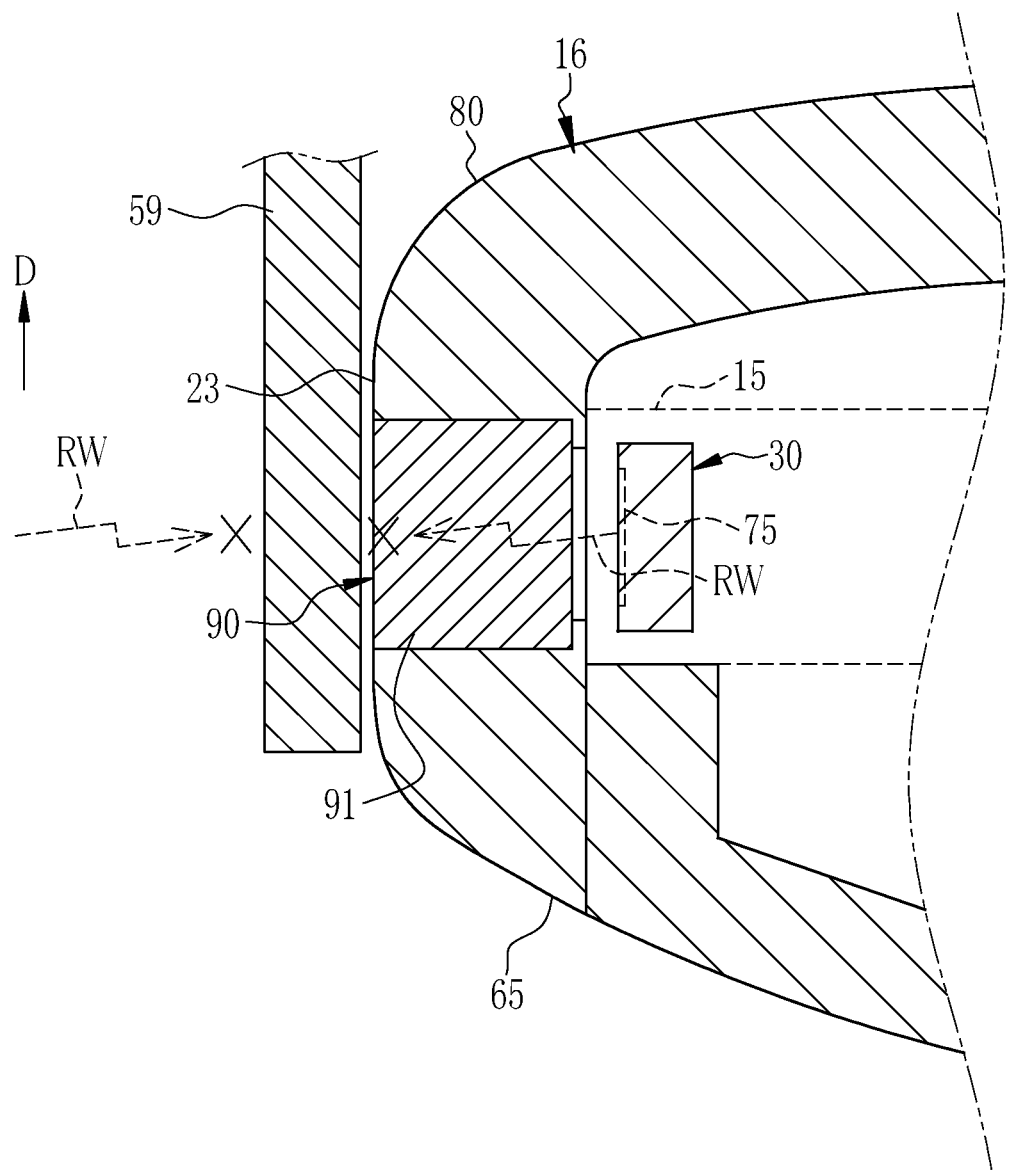
FIG. 9 is a view showing a comparative example in which an antenna opening is formed on the side surface of the housing.

Further, in the case where the antenna opening 90 is formed on the side surface 23 as in the case of the comparative example shown in FIG. 9, the strength of the side surface 23 is lower in comparison with the case where the antenna opening 90 is not formed on the side surface 23. In the case where the electronic cassette 10 is inserted into the clearance between the subject H lying on the bed and the bed to perform X-ray photography, a load of the subject His intensively applied to the side surface 23 parallel to the direction D, and therefore the low strength of the side surface 23 causes uneasiness. In contrast, in the case where the strength of the side surface 23 is secured, even if the strength of the inclined surface 65 becomes lower due to the antenna opening 66 formed on the inclined surface 65, it is possible to perform X-ray photography without constraint.

Furthermore, in the case where the strength of the side surface 23 of the housing 16 is secured, even if the electronic cassette 10 is dropped by mistake, the electronic cassette 10 is hardly damaged. The main reason why the dropped electronic cassette 10 is damaged is that the side surface 23 or the corner of the housing 16 is hit against the ground and the side surface 23 is applied with an impact. Accordingly, in the case where the strength of the side surface 23 is secured, it is possible to prevent the electronic cassette 10 from being damaged at the time of being dropped.

The antenna opening 66 is blocked by the cover 73. This allows the inclined surface 65 to be a flat surface. Thus, when the electronic cassette 10 is inserted into the clearance between the subject H lying on the bed and the bed, the antenna opening 66 is not caught on the bed, and does not interfere with the operation.

Since the antenna 75 is installed at the position facing the antenna opening 66, it is possible to further improve transmission/reception efficiency of the radio wave RW. Additionally, since the width W1 of the inclined surface 65 is made larger than the width W2 of the side surface 23, an opening area of the antenna opening 66 can be made larger in comparison with the comparative example shown in FIG. 9 in which the antenna opening 90 is formed on the side surface 23. Therefore, it is possible to further improve transmission/reception efficiency of the radio wave RW.

The provision of the inclined surfaces 65 and 80 allow the front surface 20, the rear surface 21, and the side surfaces 22 to 25 to be connected to each other by a smoothly curved surface having no corner. Therefore, the sense of touch with the housing 16 for the subject H becomes softer. Further, in the case where the electronic cassette 10 is placed on a flat surface, it is possible to lift up the electronic cassette 10 easily by putting a finger on the inclined surfaces 65 and 80. Additionally, it is possible to smoothly insert the electronic cassette 10 into the clearance between the subject H lying on the bed and the bed.

Figure 10:
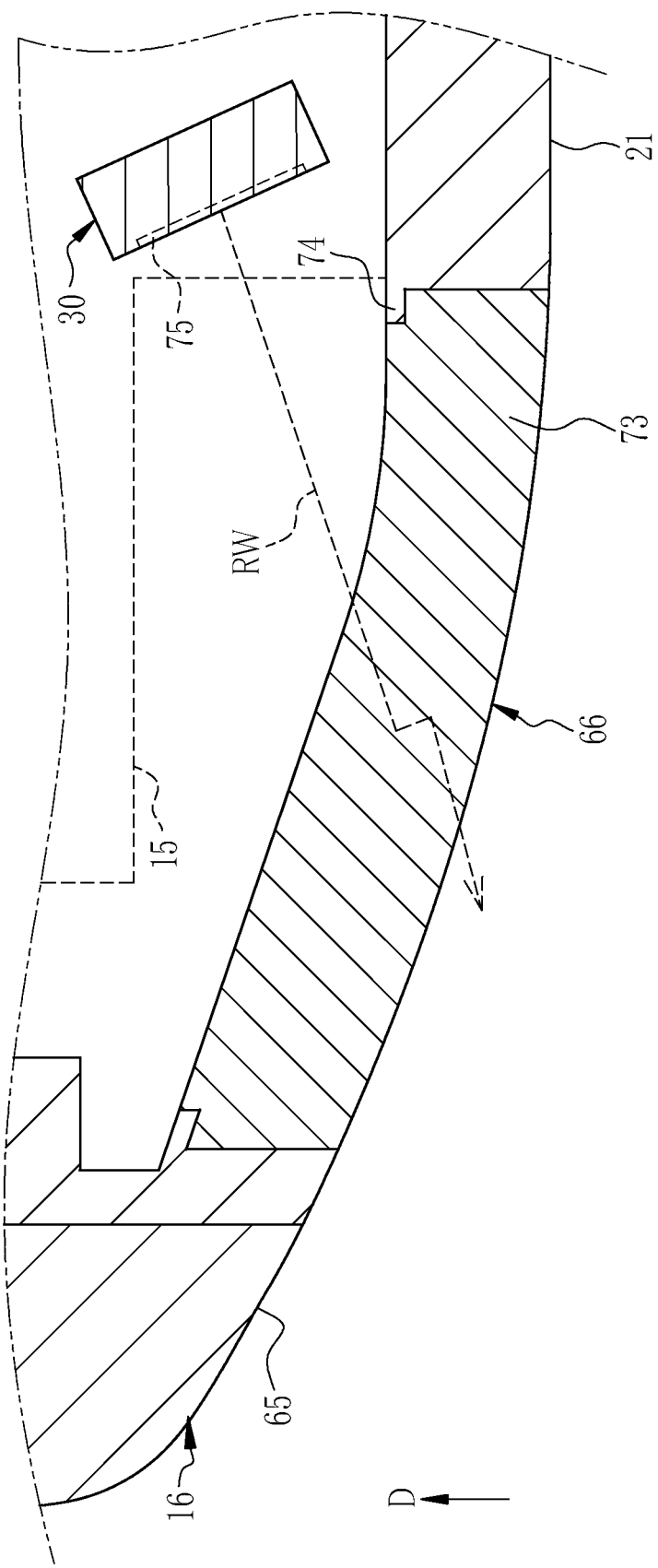
FIG. 10 is a view showing an example in which an antenna does not face the antenna opening.

Note that, the position for installing the antenna 75 is not limited to the position facing the antenna opening 66 as in the case of the above embodiment. The antenna 75 may be installed at a position deviated from the antenna opening 66 by disposing the wireless communication section 30 at a position closer to the center of the housing 16 near the rear surface 21 as viewed from a direction perpendicular to the direction D, as shown in FIG. 10, for example.

The antenna opening 66 may extend to the rear surface 21 and the side surface 23, instead of being formed only on the inclined surface 65.

Figure 11:
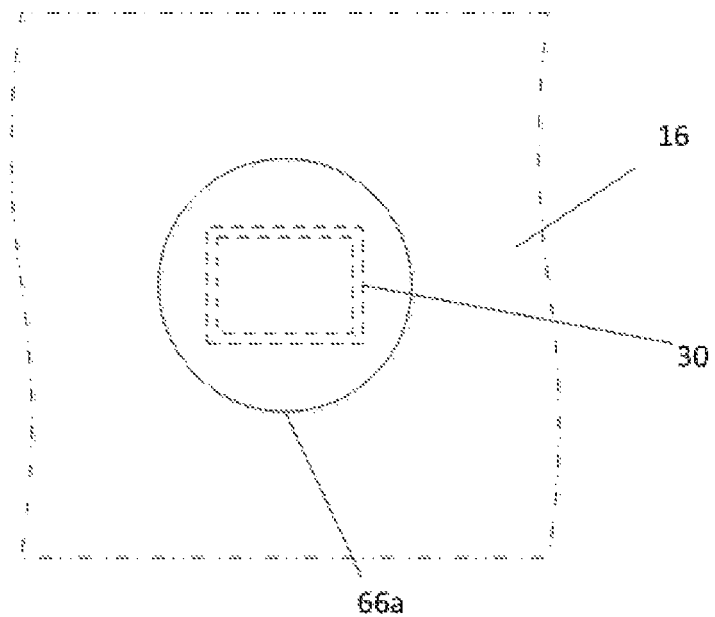
FIG. 11 is a view showing an example in which an antenna opening is a circular shape, in accordance with at least one embodiment.
Figure 12:
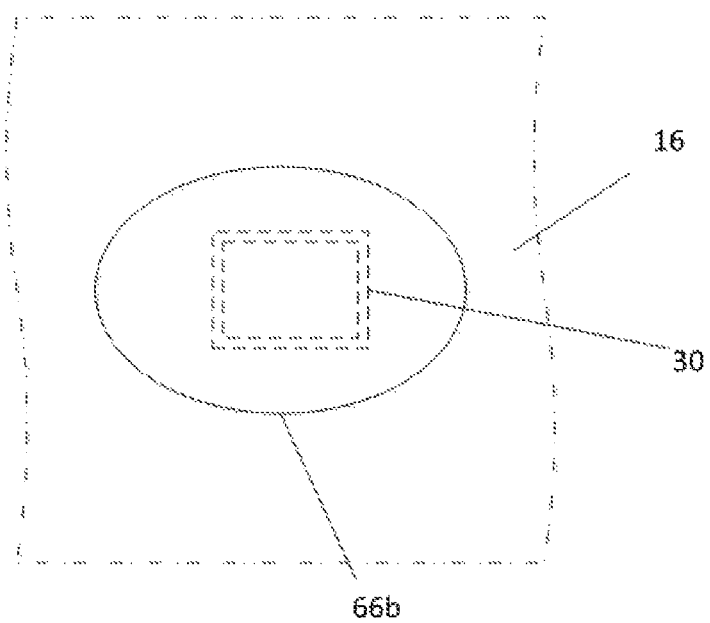
FIG. 12 is a view showing an example in which an antenna opening includes an oval shape, in accordance with at least one embodiment.

The shape of the antenna opening 66 is not limited to the rectangular shape as in the case of the above embodiment, and may be a circular shape (See FIG. 11, antenna opening 66a) or an oval shape (See FIG. 12, antenna opening 66b). Further, it is sufficient that the antenna 75 has at least a function of wirelessly transmitting the X-ray images to the control device. Furthermore, it is unnecessary for the wireless connection section 30 to consist of the antenna 75, the oscillation circuit, and the like, which are integrated together, as exemplified in the above embodiment. The wireless connection section 30 may consist of the antenna 75, the oscillation circuit, and the like, which are separated from one another.

Although the inclined surface 65 is formed between each of the side surfaces 22 to 25 and the rear surface 21 in the above embodiment, it is sufficient that the inclined surface 65 is formed at least between the side surface provided with the wireless communication section 30 and the rear surface 21.

The side panel of the outer grid is not necessarily provided for all the side surfaces 22 to 25. For example, an outer grid having a side panel provided to only the portions facing the side surfaces 22 and 23 may be used. Further, each of the inclined surfaces 65 and 80 is not limited to the curved surface which is convex toward the outside of the housing 16 as described in the above embodiment, and may be a flat surface or may be in a shape obtained by combining a curved surface and a flat surface.

Note that, without using the scintillator, a direct conversion-type image detector using a conversion layer (amorphous selenium or the like) which directly converts the X-ray into the charge may be used. Further, although the image detector of the TFT type is exemplified in the above embodiment, the present invention may adopt an image detector of a CMOS (Complementary Metal Oxide Semiconductor) type. Furthermore, the present invention is also applicable to an electronic cassette using other radiation rays such as γ-rays instead of the X-rays in radiography.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An electronic cassette comprising:
   an image detector, including an active matrix substrate, for detecting a radiation image of a subject based on radiation having been transmitted through the subject;
   a housing for housing the image detector, the housing having a front surface on which the radiation is incident, a rear surface facing the front surface, four side surfaces and an inclined portion, the inclined portion being inclined relative to at least a part of the side surfaces and a part of the rear surface, and having a first end and a second end which is opposite to the first end, the first end contacting to at least one of the side surfaces, a second end contacting to the rear surface;
   an antenna for use in wireless transmission of at least the radiation image via radio waves, the antenna being disposed inside the housing;
   an antenna opening through which the radio waves are transmitted, the antenna opening being formed only on the inclined portion; and
   a cover having a same shape and size of the antenna opening for blocking the antenna opening,
   wherein the cover and the antenna opening are bonded to each other, and
   wherein the inclined portion is provided between the rear surface and the side surfaces only.

2. The electronic cassette according to claim 1, wherein the radio waves are transmitted and received through the inclined portion.

3. The electronic cassette according to claim 1, wherein the antenna is disposed at a position which faces the antenna opening.

4. The electronic cassette according to claim 1, wherein the antenna is disposed so as to be deviated from a position which faces the antenna opening.

5. The electronic cassette according to claim 1, wherein the antenna is disposed so as to have a space from the antenna opening.

6. The electronic cassette according to claim 1, wherein the antenna opening has a rectangular shape, a circular shape or an oval shape.

7. The electronic cassette according to claim 1, wherein an opening area of the antenna opening is smaller than an area of the inclined portion.

8. The electronic cassette according to claim 1, wherein the cover is made of a non-conductive material having radio wave transmission properties.

9. The electronic cassette according to claim 1, wherein a width of the inclined portion corresponding to a distance between a first boundary that is a boundary between the side surface and the inclined portion of the housing and a second boundary that is a boundary between the rear surface and the inclined portion of the housing is larger than a width of the side surface in a thickness direction of the housing that is perpendicular to the front surface and the rear surface.

10. The electronic cassette according to claim 1 being set to be attachable to and detachable from a holder of a radiographic stand.

11. The electronic cassette according to claim 1, wherein an outer grid is detachably attached to the housing in order to remove scattered rays generated upon transmission of the radiation through the subject.

12. The electronic cassette according to claim 1, further comprising:
   a battery mounting section on which a battery for supplying electricity is mounted, the battery mounting section being a concave portion in which the rear surface is recessed toward the front surface.

13. The electronic cassette according to claim 3, wherein the antenna is disposed to be located at a center of the antenna opening, and so that an installation surface on which the antenna is installed is parallel to the inclined portion.

14. The electronic cassette according to claim 3, wherein an opening area of the antenna opening is larger than an area of a surface of the antenna, the surface facing the antenna opening.

15. The electronic cassette according to claim 10, wherein the holder including:
   a front plate for covering the front surface of the housing; and
   a rear plate for covering the rear surface of the housing, the rear plate facing the front plate.

16. The electronic cassette according to claim 11, wherein the outer grid including:
   a top panel for covering the front surface of the housing; and
   a side panel which is provided to an edge of the top panel and extends in a direction from a front-surface side of the housing toward a rear-surface side thereof so as to cover a part of the side surface of the housing.

* * * * *